United States Patent [19]

Opavsky et al.

[11] 4,311,563
[45] Jan. 19, 1982

[54] PROCESS FOR THE ISOLATION OF MONOCHLOROACETALDEHYDE

[75] Inventors: Werner Opavsky, Dumaguete City, Philippines; Josef Reisner; Alois Maier, both of Cologne, Fed. Rep. of Germany

[73] Assignee: Wacker-Chemie GmbH, Munich, Fed. Rep. of Germany

[21] Appl. No.: 249,324

[22] Filed: Mar. 31, 1981

[30] Foreign Application Priority Data

Apr. 10, 1980 [DE] Fed. Rep. of Germany ....... 3013817

[51] Int. Cl.³ .......................... B01D 3/14; C07C 47/14
[52] U.S. Cl. ........................................ 203/46; 203/71; 203/87; 568/478; 568/492; 568/495
[58] Field of Search ................... 203/71, 73, 44, 46, 203/87; 568/478, 492, 495

[56] References Cited

U.S. PATENT DOCUMENTS 2,702,783  2/1955  Harrison et al. ..................... 203/46
2,947,671  8/1960  Veldhuis et al. ..................... 568/492

FOREIGN PATENT DOCUMENTS 1130426  5/1962  Fed. Rep. of Germany .
1147211  4/1963  Fed. Rep. of Germany .

Primary Examiner—Wilbur L. Bascomb, Jr.
Attorney, Agent, or Firm—Allison C. Collard; Thomas M. Galgano

[57] ABSTRACT

The invention relates to a process for the isolation of chloroacetaldehyde which is obtained as a by-product during the synthesis of acetaldehyde from ethylene and air in an aqueous palladium/cupric chloride solution by the 2-stage process. The mixture to be worked-up to chloroacetaldehyde is taken from the acetaldehyde distillation column and transferred to a distillation and extraction system, where it is fractionally condensed. The chloroacetaldehyde-containing fraction is extracted with water and the aqueous extract is subjected to purification distillation.

3 Claims, 1 Drawing Figure

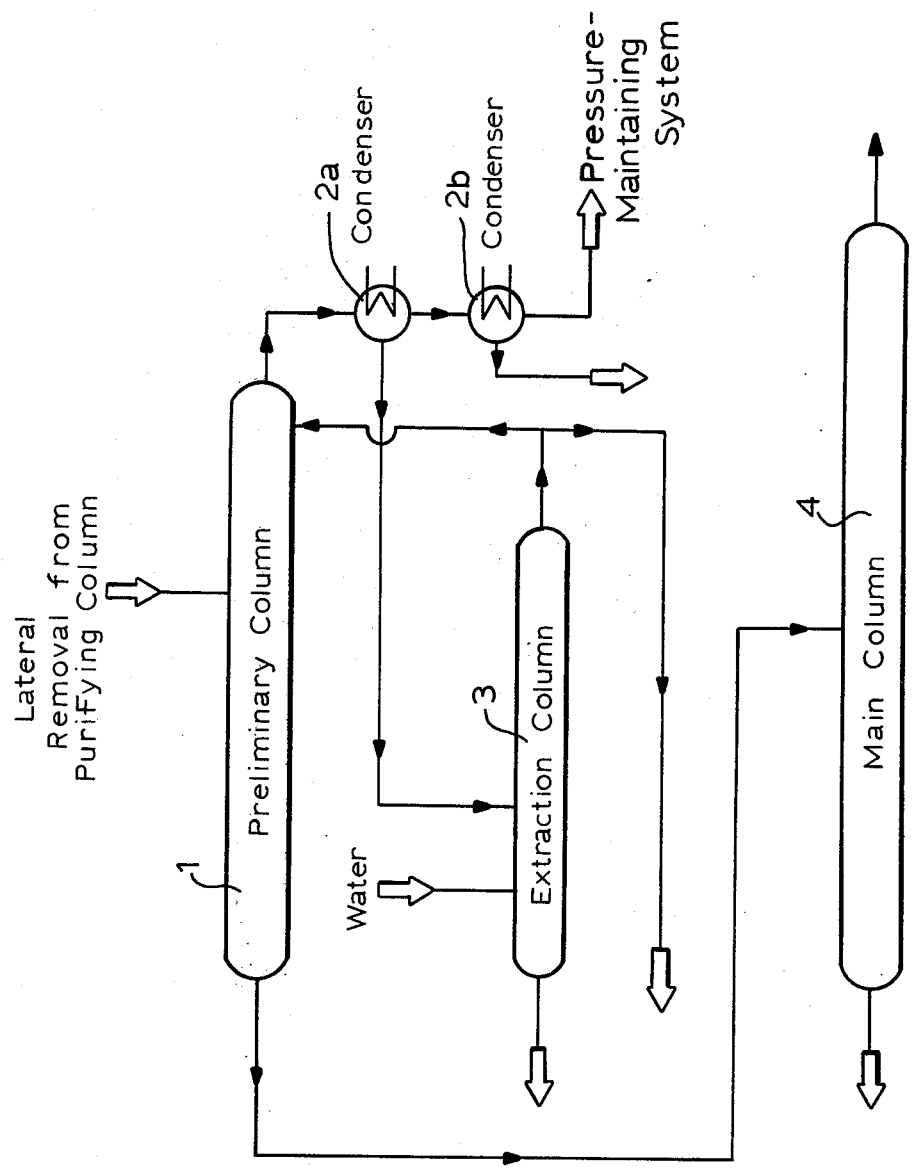

PROCESS FOR THE ISOLATION OF MONOCHLOROACETALDEHYDE

The invention relates to a process for the isolation of monochloroacetaldehyde, referred to herein as chloroacetaldehyde, which is obtained as a by-product during the synthesis of acetaldehyde from ethylene and air in an aqueous palladium chloride/cupric chloride solution by the 2-stage process, wherein crude chloroacetaldehyde is drawn from the acetaldehyde purification column and transferred to a distillation and extraction system.

The method of synthesis referred to herein as the 2-stage process (alternatively a 1-stage process may be used) is a process for the production of acetaldehyde from ethylene and air in an aqueous palladium chloride/cupric chloride solution, in which the conversion of the ethylene to acetaldehyde and the oxidative regeneration reaction of the catalyst are carried out in separate reactors (cf. on this point *Ullmanns Enzyklopädie der Technischen Chemie*, 4th Edition, 1974, pp. 16–18, Weinheim/Bergstrasse).

In the above-mentioned 2-stage process, by-products amounting to about 4% of the converted ethylene are formed, about 1.5% of those, based on the ethylene, being chlorinated aldehydes and, in particular, chloroacetaldehyde.

The removal of the chlorinated aldehydes during the purifying distillation of the acetaldehyde is described in German Pat. No. 11 47 211. It is expediently carried out by removal from the acetaldehyde purification column at a lateral outlet.

German Auslegeschrift No. 11 30 426 describes the separation of chloroacetaldehyde from mixtures of chloroacetaldehyde, dichloroacetaldehyde and trichloroacetaldehyde.

The aqueous mixture obtained from the lateral outljet, and referred to herein as crude chloroacetaldehyde, contains not only chlorinated acetaldehydes, but also α-chlorocrotonaldehyde, chlorofuran, acetaldehyde, ethanol and smaller quantities of chloroform and methylene chloride. In a 2-stage distillation system, the aqueous mixture is worked-up to chloroacetaldehyde, with the low-boiling fractions, consisting of α-chlorocrotonaldehyde and chlorofuran, being separated at the head of a preliminary column, while, in the second column, chloroacetaldehyde of 70 to 80% strength is drawn off at the head of the column and dichloroacetaldehyde and trichloroacetaldehyde are removed via the still.

In that method, between 30 and 60% of the chloroacetaldehyde removed from the acetaldehyde purification column can be isolated. The relatively low yield is due to the high head losses of chloroacetaldehyde in the preliminary column, but, because of its distillation behavior, that cannot be avoided if adequate separation of acetaldehyde, α-chlorocrotonaldehyde and chlorofuran is to be achieved.

The object of the invention was therefore to increase the yield of chloroacetaldehyde obtained during the synthesis of acetaldehyde by the 2-stage process and, at the same time, to cleanse the waste water resulting from the process.

This object is achieved by the process according to the invention. The process is characterized in that:

(a) crude chloroacetaldehyde is fed to a distillation column;

(b) the head product from the column is fractionally condensed;

(c) the chloroacetaldehyde and by-products-containing fraction is extracted with water; and (d) the aqueous extract is worked-up by distillation to chloroacetaldehyde.

It is preferable to take the following additional measures:

(1) return the acetaldehyde-containing fraction obtained during fractional condensation to the acetaldehyde purification column;

(2) add the chloroacetaldehyde-containing aqueous extract again to the column, as per (a) above; and (3) subject the sump product of the column to purification distillation.

Furthermore, it is particularly preferable to divide the aqueous, chloroacetaldehyde-containing extract into two parts, returning the major part to the column and discarding the lesser part.

The product to be worked-up to chloroacetaldehyde, described below as crude chloroacetaldehyde, is removed from the acetaldehyde purification column. The point at which it is removed from the column depends on the dimensions and separation performance and on the loading of the column. It is expedient to discharge it at the point where the concentration of chloroacetaldehyde is highest. Since chloroacetaldehyde is, however, spread over a fairly wide region of the column, especially when using a method of operation designed for high throughput quantities, it is often advantageous to remove it from several outlets and possibly also from the still outlet of the column.

Crude chloroacetaldehyde is obtained as an aqueous mixture of more or less the following typical composition, the water content bringing it up to 100% (the figures are percent by weight):

0.5–3%, acetaldehyde;
3–15%, chloroacetaldehyde;
1–5%, dichloroacetaldehyde;
approx. 1%, trichloroacetaldehyde;
approx. 1%, α-chlorocrotonaldehyde;
up to 0.5%, ethanol;
up to 0.5%, crotonaldehyde; and traces of methylene chloride, chloroform and chlorofuran.

The further treatment of the mixture will be explained in greater detail with reference to the drawing, which depicts a flow diagram of the inventive process.

The above-defined mixture is continuously fed to a distillation column 1 (the preliminary column in the drawing), which generally contains filling material, such as glass or ceramic rings. It is connected to a device for fractional condensation of the distillate, for example, two head condensers 2a, 2b connected in series. The fractional condensation of the column product is controlled in such a way that the major part of the acetaldehyde passes through the first head condenser and is not extracted until the next condensation step, and, in an advantageous embodiment of the process, is returned to the acetaldehyde purification column.

The presence of acetaldehyde does not therefore have to be considered when further treating the chloroacetaldehyde-containing fraction obtained as partial condensate at the first head condenser 2a. That partial condensate is transferred to an extraction column 3 and extracted with water, preferably countercurrently. The water-insoluble constituents, in particular chlorofuran and α-chlorocrotonaldehyde, accumulate as the denser organic phase in the base or sump of the extraction column and are thus removed from the system.

The water-soluble constituents, in particular the chlorinated aldehydes, and also ethanol and crotonaldehyde, are returned from the overflow of the extraction column, in a cyclical process to preliminary column 1. It is preferable to divide those aqueous extracts, with approximately 90% of the partial flow being returned to column 1 and approximately 10% being removed from the system. A gradual increase in the concentration of ethanol or crotonaldehyde in a continuous process is thus prevented.

The initially purified crude chloroacetaldehyde, which, at this stage, contains substantially only the higher-chlorinated acetaldehydes, is drawn from the base of the preliminary column 1 and conveyed to a second distillation column 4 (the main column, according to the drawing), where chloroacetaldehyde is finally concentrated in a manner known per se and, at the same time, freed from dichloroacetaldehyde and trichloroacetaldehyde.

The process is generally carried out in the region of atmospheric pressure. Depending on the loading of the columns and on the basis of the hydrostatic pressure gradient within the columns, a pressure range of from 0.8 to 2.2 bar absolute is produced. If desired, however, higher or lower pressures may be used, a range of from 0.5 to 5 bar absolute being considered technically suitable.

The temperatures in the distillation units are from 60° to 120° C. and, preferably from 75° to 95° C. The temperatures in the extraction unit are from 7° to 40° C. and, preferably from 15° to 30° C.

The process according to the invention permits the isolation of chloroacetaldehyde in high yields. Thus, while at the same time cleansing the waste water resulting from large-scale acetaldehyde production, a by-product which in itself is undesirable is put to an economically sensible further use as the starting material for chemical intermediate products. In addition, impurities such as α-chlorocrotonaldehyde, which has a very adverse effect on the storage life of chloroacetaldehyde, are totally eliminated. By the process according to the invention, it is also possible to concentrate within the system further by-products occurring in fairly small quantities and thus for the first time create the preconditions necessary for eliminating such harmful substances without polluting the waste water, for example by burning. Furthermore, there is an appreciable reduction in the loss of acetaldehyde in the overall production method.

The process according to the invention thus not only achieves more economical utilization of the entire apparatus for acetaldehyde production, but also fulfills current environmental demands.

The invention will now be explained in greater detail with the aid of the following examples and comparison examples.

EXAMPLE 1

An aqueous mixture of the following composition:
35 g/l chloroacetaldehyde;
27 g/l acetaldehyde;
13 g/l α-chlorocrotonaldehyde;
2 g/l ethanol;
2 g/l chlorofuran;
1 g/l chloroform;

in addition to dichloroacetaldehyde and trichloroacetaldehyde is removed as a lateral discharge, at a pressure of 1.1 bar absolute and a temperature of 85° C., from the acetaldehyde purification column. This mixture containing chloroacetaldehyde is fed to the distillation column, measured at the column inlet, at the rate of 31.5 kg per hour. The top-product of the column is fractionally condensed, and the partial condensate occurring at the first column head at 70° C. and 1 bar absolute pressure is extracted with water at 30° C., with 90% of the water extract being returned to the column, and 10% being removed from the system. 24 kg per hour of chloroacetaldehyde is obtained at the outlet of the column.

COMPARISON EXAMPLE 1

The procedure of Example 1 is repeated with the variation that the partial condensate is returned to the preliminary column without extraction with water.

15 kg per hour of chloroacetaldehyde was obtained at the outlet of the column.

The loss of chloroacetaldehyde in the method according to Example 1 is 9 kg per hour less than in the method of the comparison example, which corresponds to 45%.

EXAMPLE 2

A lateral discharge of the following composition:
5.1% by weight of chloroacetaldehyde;
1.1% by weight of acetaldehyde;
1.2% by weight of α-chlorocrotonaldehyde;
0.6% by weight of chlorofuran; and
1.7% by weight of dichloroacetaldehyde, trichloroacetaldehyde and ethanol
with the water content making up the 100%, is worked-up in the same way as in Example 1. The throughput of chloroacetaldehyde, measured at the column inlet, is 46 kg per hour. 36 kg per hour of chloroacetaldehyde is obtained at the column outlet. In the subsequent purifying distillation phase, 34 kg per hour of pure chloroacetaldehyde is obtained.

COMPARISON EXAMPLE 2

The lateral removal according to Example 2 is worked-up without extraction with water. 27 kg per hour of chloroacetaldehyde is obtained. In the subsequent purifying distillation step, 25 kg per hour of chloroacetaldehyde is obtained.

Comparing Example 2 with Comparison Example 2, the overall yield of chloroacetaldehyde is increased by 36%.

Thus, while only several examples of the present have been shown and described, it will be obvious that many changes and modifications may be made thereunto, without departing from the spirit and scope of the invention.

What is claimed is:

1. A process for the isolation of chloroacetaldehyde, which is obtained as a by-product during the synthesis of acetaldehyde from ethylene and air in aqueous palladium chloride/cupric chloride solution by the 2-stage process, wherein crude chloroacetaldehyde is drawn from the acetaldehyde purification column and transferred to a disillation and extraction system, comprising the steps of:
   (a) feeding crude chloroacetaldehyde to a distillation column and distilling the same to produce a head distillation product;

(b) fractionally condensing the head product to produce a chloroacetaldehyde-containing fraction;

(c) extracting the chloroacetaldehyde-containing fraction with water to produce an aqueous extract; and (d) distilling said aqueous extract to produce chloroacetaldehyde.

2. The process according to claim 1, wherein said step (b) also produces an acetaldehyde-containing fraction and wherein said process additionally includes the steps of:

(e) returning said acetaldehyde-containing fraction to the acetaldehyde purification column;

(f) returning at least a portion of said aqueous extract obtained from said step (c) to said column for redistillation and extraction with said crude chloroacetaldehyde according to steps (a) and (b); and (g) subjecting the sump product obtained from the column according to steps (a) and (f) to purification distillation.

3. The process according to claim 2, additionally including the step of dividing the aqueous extract obtained by step (c) into a greater part and a smaller part and feeding the greater part to the column according to step (a) and removing said smaller part from said system.

* * * * *